United States Patent [19]
Baldwin

[11] Patent Number: 5,486,692
[45] Date of Patent: Jan. 23, 1996

[54] GLASSWARE INSPECTION MACHINE COMPRISING DIFFUSED LIGHT SOURCES AND TWO-DIMENSIONAL CAMERAS

[75] Inventor: Leo B. Baldwin, Horseheads, N.Y.

[73] Assignee: Emhart Glass Machinery Investments Inc., Wilmington, Del.

[21] Appl. No.: 325,770

[22] Filed: Oct. 19, 1994

[51] Int. Cl.⁶ .................................................. G01N 21/90
[52] U.S. Cl. ....................... 250/223 B; 356/240; 209/526
[58] Field of Search ........................ 250/223 B; 356/240; 209/524, 526; 348/92, 127, 128

[56] References Cited

U.S. PATENT DOCUMENTS

| | | | |
|---|---|---|---|
| 4,025,201 | 5/1977 | Deane | 250/223 B |
| 4,280,624 | 7/1981 | Ford | 250/223 B |
| 4,367,405 | 1/1983 | Ford | 250/223 B |
| 4,509,081 | 4/1985 | Peyton et al. | 250/223 B |
| 4,625,107 | 11/1986 | Planke | 250/223 B |
| 4,636,635 | 1/1987 | Krönseder | 250/223 B |
| 4,948,956 | 8/1990 | Fukuchi | 250/223 B |
| 5,216,481 | 6/1993 | Minato | 250/223 B |
| 5,256,871 | 10/1993 | Baldwin | 250/223 B |

*Primary Examiner*—Edward P. Westin
*Assistant Examiner*—John R. Lee

*Attorney, Agent, or Firm*—Spencer T. Smith

[57] ABSTRACT

An inspection machine for inspecting a vertically standing container comprising a conveyor for horizontally displacing a vertically standing glass container through spaced inspection locations, a first pair of diffused light sources located behind the conveyor for forwardly directing angularly related beams of light substantially horizontally at a container located at one of the inspection locations, the beams being sufficiently large so that the light beams will pass around the entire profile of a container located at the first inspection location, a first two dimensional camera having an imaging surface on the other side of the conveyor, and first means for redirecting the forwardly directed beams to corresponding halves of the imaging surface, a second pair of diffused light sources located in front of the conveyor for rearwardly directing angularly related beams of light substantially horizontally at a container located at the other one of the inspection locations, the beams being sufficiently large so that the light beams will pass around the entire profile of a container located at the other inspection location, a second two dimensional camera having an imaging surface on the side of the conveyor opposite to the second pair of diffused light sources, second means for redirecting the rearwardly directed light beams to corresponding halves of the imaging surface of the second two dimensional camera, and means for analyzing the sidewall image in each half of each image sensor.

8 Claims, 2 Drawing Sheets

GLASSWARE INSPECTION MACHINE COMPRISING DIFFUSED LIGHT SOURCES AND TWO-DIMENSIONAL CAMERAS

FIELD OF THE INVENTION

Glass containers are made in glass forming machines from discrete gobs of molten glass. Many things can happen during this formation process which can adversely effect the formed container. Using a soda bottle as an example, the formed bottle may have a profile defect (it may improperly tilt or lean from its vertical axis) or it may have a wall defect such as a bubble or an inclusion.

DESCRIPTION OF RELATED ART

To identify containers having these or other profile defects (cocked finish, bent, base leaner, diameter variation, freak), the entire profile of the container is inspected. U.S. Pat. No. 5,256,871 discloses a machine which can dimensionally gauge a container to determine profile faults.

In state of the art machines, inspection must take place at the rate of up to 600 bottles per minute which is 10 containers per second. When a camera is used in the inspection process only a single image is available for evaluation and accordingly, a single camera has been dedicated to a single inspection such as the above-described dimensional gauging.

It is an object of the present invention to provide an inspection system which will simultaneously inspect for profile and wall faults.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWING

Referring to the drawings.

DESCRIPTION OF THE PREFERRED EMBODIMENT

Figure 1:
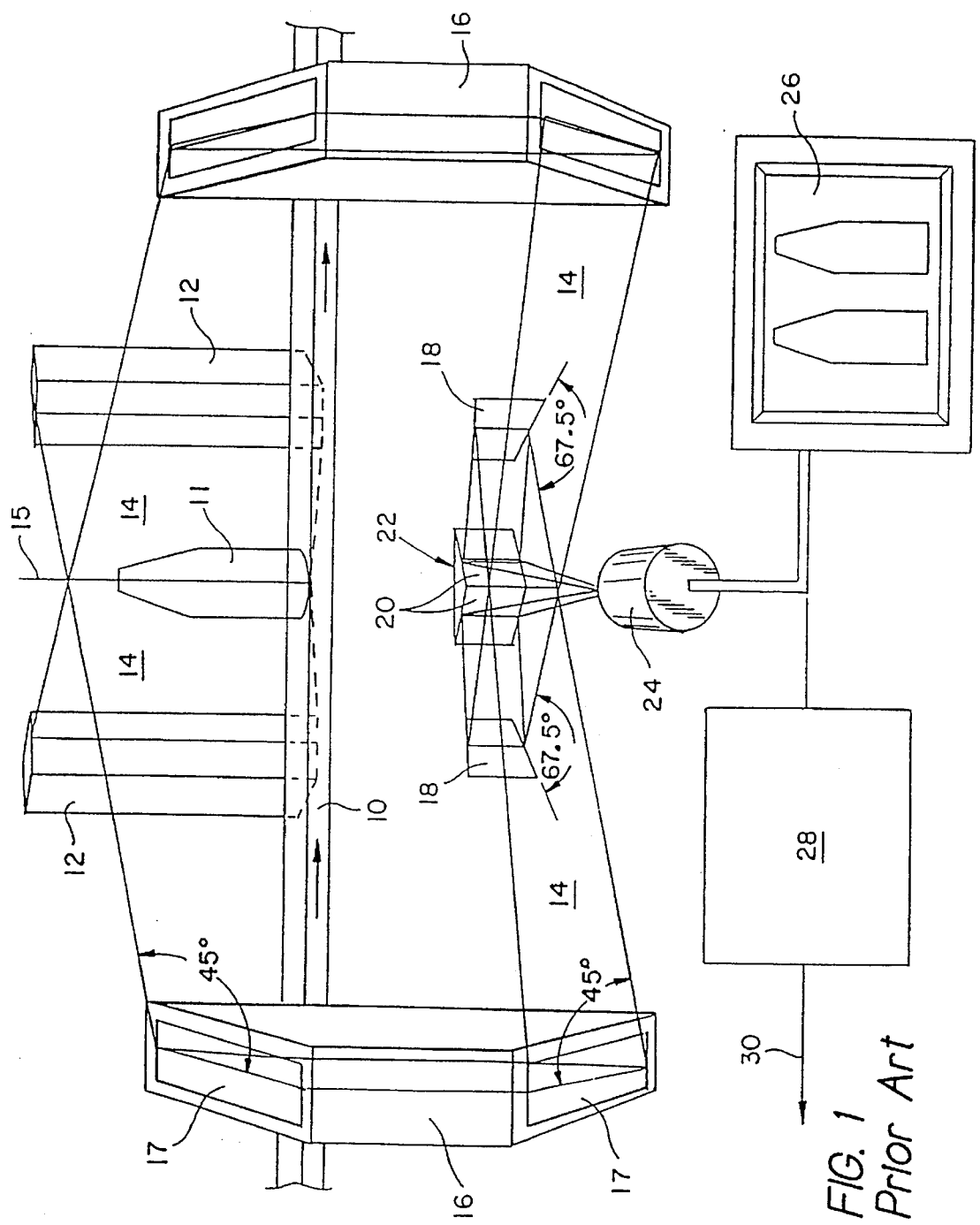
FIG. 1 discloses an oblique schematic view of an inspecting machine made in accordance with the prior art.

A horizontal conveyer 10, moving at a constant speed carries a vertically standing glass container (a bottle) 11 through the illustrated inspection location. At this location a pair of light sources 12 which can be short arc flash tube strobes and which are located behind the conveyor direct diffused back light horizontally, past the bottle at an angle of approximately 45° to the conveyor. As a result, these beams 14 of diffused light intersect perpendicularly through the vertical axis 15 of the bottle when it is located at the inspection location. These beams are larger than the largest container to be inspected so that light will always pass around the entire profile (the sides and top) of a container located at the inspection location. The light from each source is beamed to vertically related mirror pairs 16 which are located in front of the conveyor and which horizontally return the beams to redirecting mirrors 18. The mirrors 17 of these mirror pairs receive these light beams at an angle of approximately 45° (relative to a normal ray). The redirecting mirrors redirect the beams to the reflecting surfaces 20 or a reflecting prism 22 which aim the beams to a corresponding half of the image of a two-dimensional camera 24. Both the redirecting mirrors 18 and the reflecting surfaces 20 of the prism 22 also receive these light beams at an angle of no more than 45° (23.5° and 45° respectively). By configuring the light beam path so that the beam strikes each reflecting surface at no more than about 45° (to a normal ray), unwanted polarization effects will be avoided. And all structures can be located within a very compact footprint. Both images can be presented on a suitable screen 26 and can be evaluated by an image processing computer 28 which can evaluate both views. This image processing computer will issue an acceptance or rejection signal 30. Additional details are set forth in U.S. Pat. No. 5,256,871, which are incorporated herein.

Figure 2:
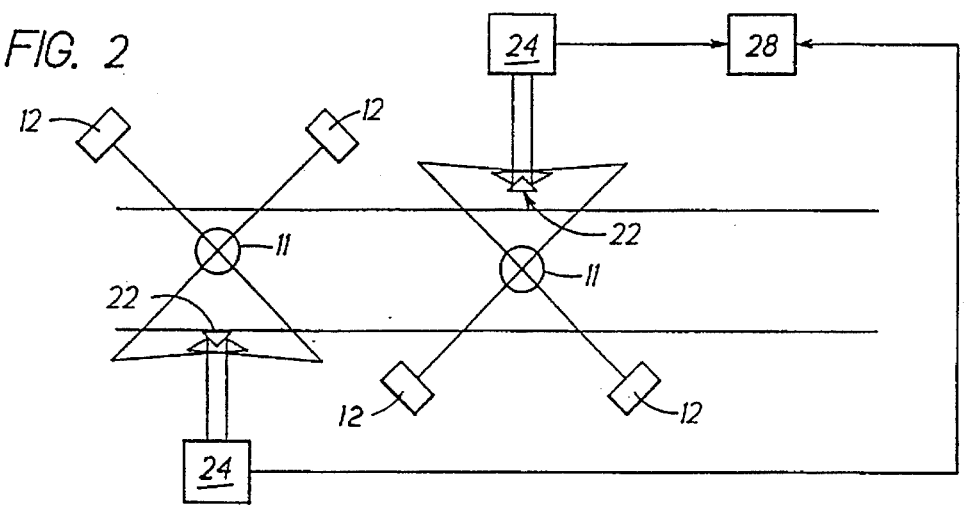
FIG. 2 schematically shows a duplex system made in accordance with the teachings of the present invention.

As shown in FIG. 2, the preferred embodiment is a duplexed version of the prior art system shown in FIG. 1 with one pair of 90° related light sources 12 being located on one side of the conveyor with the image sensor 24 on the opposite side and with a second pair of 90° related light sources and their associated image sensor being arranged just the opposite.

Figure 3:
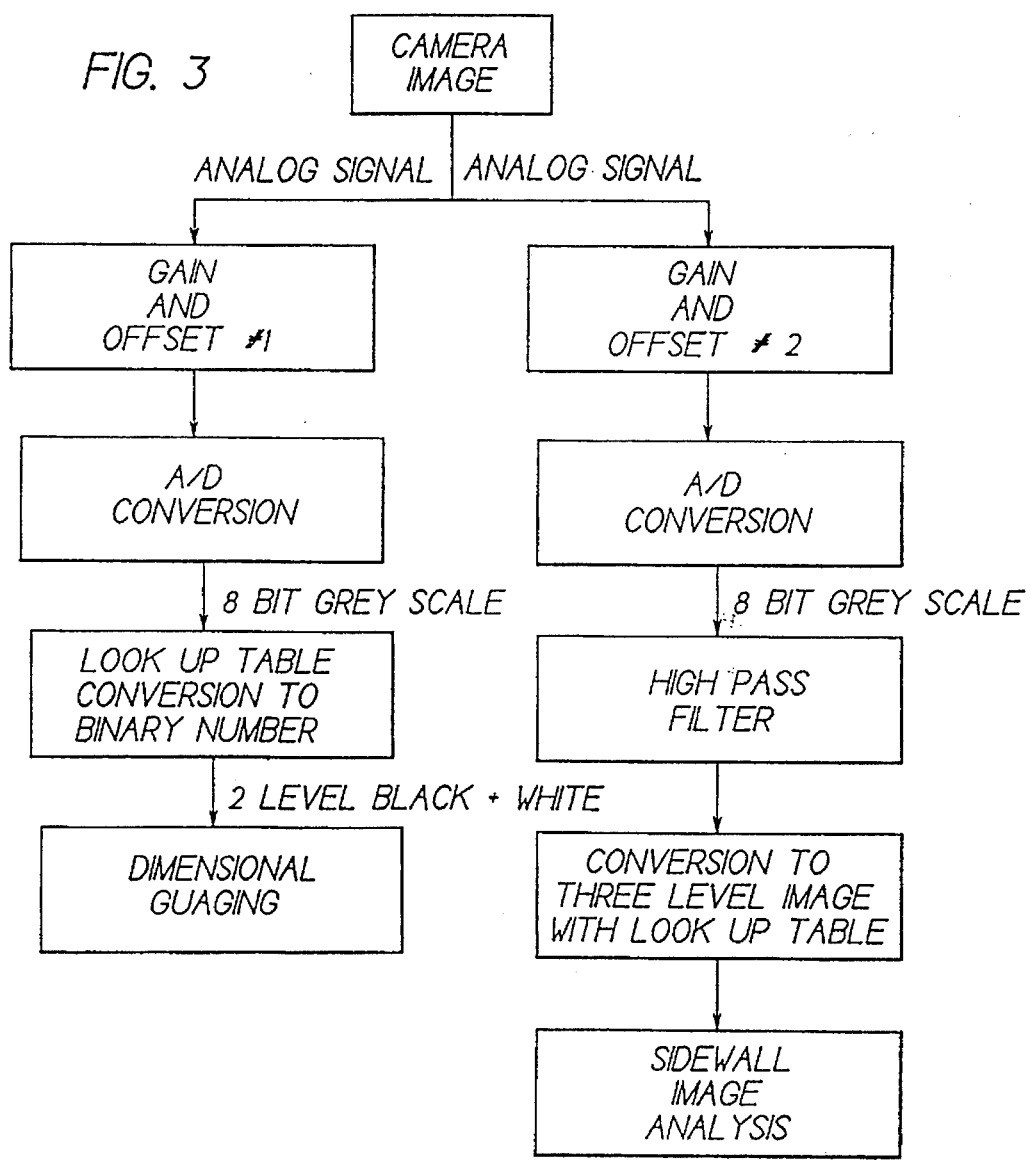
FIG. 3 shows a flow chart of the disclosed inspection algorithm.

The inspection algorithm for each of the four light paths is shown in FIG. 3. The image on the camera sensor (a pixel array) is simultaneously supplied to dimensional gaging and sidewall analysis channels. Analysis of the sidewall image is accordingly performed simultaneously with the dimensional gauging. This method has benefits in both speed and image quality. The gain and offsets for the sidewall image analysis channel (Gain and Offset #2) optimized separate from the gain and offset for the dimensional gauging channel (Gain and Offset #1) since the image requirements for each channel are distinct. Dimensional gauging requires an optimal transition at the edge between the bottle image and its background. For heavily colored bottles this setup can leave the sidewall image rendered with a very low dynamic range. Conversely, sidewall analysis requites that the container sidewall (at least the center half) be imaged with maximum dynamic range, even if this requirement puts the background image into saturation and obscures the edge of the container image. Typically, lighting, lens aperture, zoom, focus, converter gain and converter offset will be optimized for sidewall acquisition. Once optimum sidewall imaging is obtained, the gain and offset for the channel corresponding to the dimensional gauge image are adjusted for optimal edge rendition. Gains and offsets are set electronically without user intervention. Aperture focus and zoom can be set by the user in response to prompts provided by the inspection device's user-interface.

With Gain and Offset #1 set for the dimensional gauging channel, the analog signal will be converted from analog to digital form (8 bit gray scale) and a look up table will convert the digital signal to a two level black and white signal that can be used by the controller to perform dimensional gauging. For example, since the edges of the bottle can be located bottle width and the existence of tilt, etc. can be determined.

With Gain and Offset #2 set for the sidewall analysis channel, the same analog signal will be converted from analog to digital form (8 bit gray scale). The 8 bit gray scale image is subjected to high pass filtering and the high pass filtered image is then thresholded into a three-level 8 bit image by user selectable zone. A three level image is used to preserve the optical quality of the defect: opaque or transparent. The size and position of the zones are selected by the user to permit different sensitivity adjustments for different parts of the container. After thresholding, all but the center half plus a slight allowance for overlap of the four container images is masked to match the intensity of the nominal container sidewall. One half of the image corresponds to the 90° covered by each view, and the allowance ensures that a defect which lies on the boundary between two views does not escape detection. The masking eliminates false artifacts arising from the container edges and specular reflections from the area outside the inspection area (for example, from the backlight for the other view).

After masking, the total number of defect pixels in each zone, which are polarized by the thresholding process, are summed into a pair of values, one for each polarity. Each polarity is then evaluated by separate criteria for container acceptance or rejection. One polarity will correspond to stones, which are opaque. The other polarity will correspond to bubbles. A group of values of both polarities generally corresponds to a refractive defect such as wrinkle, wave or bird swing, although it could correspond to a stone and a bubble in close proximity.

I claim:

1. An inspection machine for inspecting a vertically standing container comprising
    a conveyor for horizontally displacing a vertically standing glass container through spaced first and second inspection locations,
    a first pair of diffused light sources located behind said conveyor for forwardly directing 90° angularly related first and second beams of light substantially horizontally at a container located at one of said inspection locations, said first and second beams being sufficiently large so that said light beams will pass around the entire profile of a container located at said first inspection location,
    a first two dimensional camera having a first imaging surface on the other side of said conveyor for issuing an analog signal representing the image on said imaging surface, and
    first means for redirecting said forwardly directed beams to corresponding halves of said imaging surface,
    a second pair of diffused light sources located in front of said conveyor for rearwardly directing 90° angularly related third and fourth beams of light parallel substantially horizontally at a container located at the other one of said inspection locations, said third and fourth beams being parallel to said first and second beams and being sufficiently large so that said light beams will pass around the entire profile of a container located at said second inspection location,
    a second two dimensional camera having a second imaging surface on the side of said conveyor opposite to said second pair of diffused light sources for issuing an analog signal representing the image on said second imaging surface,
    second means for redirecting said rearwardly directed third and fourth light beams to corresponding halves of the imaging surface of said second two dimensional camera, and
    means for analyzing the analog signal from each of said cameras.

2. An inspection machine according to claim 1, wherein said analyzing means comprises a sidewall image analysis channel for receiving said signals including
    means for defining a selected gain and offset for said analog signals and
    means for converting the gained and offset analog signal to a digital gray scale signal.

3. An inspection machine according to claim 2, wherein said analyzing means further comprises
    means for high pass filtering said digital gray scale signal and
    means including a look up table for converting said high pass filtered digital gray scale signal to a three level image.

4. An inspection machine for inspecting a vertically standing container comprising
    a conveyor for horizontally displacing a vertically standing container through an inspection location,
    a diffused light source for directing a beam of light at a container at said inspection location, said beam being sufficiently large so that said light beam will pass around the entire profile of a container located at said inspection location,
    a two dimensional camera for sensing the image of the container at said inspection location and for issuing an analog signal defining said image and
    computer means for evaluating the dimensions and the sidewall of the container at said inspection analog location, said computer means including
    a first dimensional gauging channel having means for defining a first selected gain and offset, and
    a second sidewall image analysis channel having means for defining a second selected gain and offset,
    said first and second channels receiving the same analog signal from said camera.

5. An inspection machine according to claim 4, wherein said first dimensional gauging channel further comprises A/D conversion means for converting the gained and offset analog signals to a digital gray scale signal.

6. An inspection machine according to claim 5, wherein said second sidewall image analysis channel further comprises A/D conversion means for converting the gained and offset analog signals to a digital gray scale signal.

7. An inspection machine according to claim 6, wherein said first dimensional gauging channel further comprises means for converting the digital gray scale signal to a binary image signal.

8. An inspection machine according to claim 7, wherein said second sidewall image analysis channel further comprises
    means for high pass filtering said digital gray scale signal and
    means including a look up table for defining a three level digital image signal.

* * * * *